United States Patent [19]

Plummer

[11] 4,426,524
[45] Jan. 17, 1984

[54] HETEROCYCLIC SUBSTITUTED BENZYL ALCOHOL, INSECTICIDAL ESTER DERIVATIVES, AND INTERMEDIATES

[75] Inventor: Ernest L. Plummer, North Tonawanda, N.Y.

[73] Assignee: FMC Corporation, Philadelphia, Pa.

[21] Appl. No.: 341,361

[22] Filed: Jan. 21, 1982

Related U.S. Application Data

[62] Division of Ser. No. 183,550, Sep. 2, 1980.

[51] Int. Cl.$^3$ ................. C07D 241/00; C07D 241/02; C07D 211/70
[52] U.S. Cl. .................................. 544/336; 544/409; 549/78; 549/497; 546/344; 424/250; 424/263; 424/275; 424/285
[58] Field of Search ................. 549/78, 497; 544/336, 544/409; 546/344

[56] References Cited

U.S. PATENT DOCUMENTS

| | | |
|---|---|---|
| 3,850,977 | 11/1974 | Itaya et al. |
| 4,024,163 | 5/1977 | Elliott et al. |
| 4,130,657 | 12/1978 | Plummer |
| 4,151,293 | 4/1979 | Stein |
| 4,214,004 | 7/1980 | Plummer |
| 4,238,505 | 12/1980 | Engel |
| 4,332,815 | 6/1982 | Engel ................................ 549/79 |

FOREIGN PATENT DOCUMENTS

3336A2 8/1979 European Pat. Off.
2724494 12/1977 Fed. Rep. of Germany.

OTHER PUBLICATIONS

Derwent Abstract 88:120971f, accession #88582Y, abstract of Ger. Offen. 2,724,494, (ref AL above).
Gomberg and Bachmann, J. Am. Chem. Soc., 46, 2339, (1924).
Kosak et al., J. Am. Chem. Soc., 76, 4450, (1954).
Organic Reactions, 2, 224, (1944), pp. 236, 237, 248, 260 and 261.
Synthetic Pyrethroids, ACS Symposium Series, No. 42, M. Elliott, Ed., Am. Chem. Soc., Washington, D.C., 1977, Chapter 1.
Synthetic Pyrethroids, Ibid, Chapter 4.

Primary Examiner—Alan Siegel
Attorney, Agent, or Firm—Robert M. Kennedy; H. Robinson Ertelt; Robert L. Andersen

[57] ABSTRACT

Disclosed and exemplified are insecticidal and acaricidal optionally substituted furylbenzyl, thienylbenzyl, pyrazinylbenzyl, or pyridinzylbenzyl esters of the pyrethroid acids, novel pyrethroid alcohols and other intermediates, and compositions, a method of use and a process for preparation of the esters.

3 Claims, No Drawings

HETEROCYCLIC SUBSTITUTED BENZYL ALCOHOL, INSECTICIDAL ESTER DERIVATIVES, AND INTERMEDIATES

This application is a division of application Ser. No. 183,550, filed Sept. 2, 1980.

The present invention is directed to a novel alcohol and other intermediates for use in preparing pyrethroid and related insecticidal esters, to insecticidal esters of the alcohol, and to an insecticidal method and composition. More particularly, the invention is directed to insecticidal optionally substituted furylbenzyl, thienylbenzyl, pyrazinylbenzyl, or pyridinylbenzyl esters of certain cyclopropanecarboxylic acids and to intermediates for use in preparing them.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1). These two alcohols are representative of a common structural type characterized as being comprised of two ring systems connected to each other by an —O—, —S—, —CH$_2$—, or —CO— linkage.

A more recent advance in alcohol research was the discovery by Plummer that the connecting unit —O— between the two phenyl rings in 3-phenoxybenzyl alcohol was not essential for high insecticidal activity. In U.S. Pat. No. 4,130,657, Plummer discloses various [1,1'-biphenyl]-3-ylmethyl 3-(2,2-dihaloethenyl)-2,2-dimethylcyclopropanecarboxylates as potent insecticides and acaricides.

As a result of extensive studies, a new series of novel benzyl alcohols having an optionally substituted furan, thiophene, pyrazine, or pyridine ring attached directly to the phenyl ring of the benzyl group has been developed. The novel alcohols produce highly potent insecticidal esters when chemically combined with an appropriate acid.

The following definitions are applicable throughout the specification and claims of this application except where a different meaning is clearly indicated:

The term lower as applied to an aliphatic group or the aliphatic portion of a group, as in "lower alkyl" or "lower alkoxy", means a straight or branched chain aliphatic group or portion of a group having 1 to 6 carbon atoms, preferably 1 to 4 carbon atoms. The term "halo" or "halogen" means bromine, chlorine, or fluorine.

The novel alcohols and insecticidal esters of this invention have the general formula I

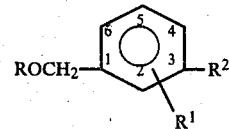

wherein R$^1$ is hydrogen, halogen preferably fluorine, lower alkyl preferably methyl, or trihalomethyl preferably trifluoromethyl; R$^2$ is a thiophene, furan, pyrazine, or pyridine ring which may be substituted with one or more halogen atoms or lower alkyl groups; and R is hydrogen, 2,2,3,3-tetramethylcyclopropylcarbonyl, 1-(4-chlorophenyl)-2-methylpropyl-1-carbonyl, or a cyclopropanecarbonyl group of the formula:

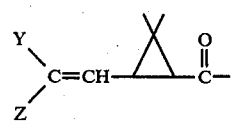

wherein one of Y and Z is halogen, and the other is halogen or perhaloalkyl of 1 or 2 carbon atoms.

Alcohols of especial interest are those of formula I (R is hydrogen) wherein the covalent bond connecting the heterocyclic group R$^2$ to the phenyl ring is from C-3 of the phenyl ring to C-2 or C-3, preferably C-2, of the heterocyclic ring (see Table I). Alcohols of particular merit within this subgenus are those in which R$^1$ is other than hydrogen, preferably methyl, and is situated at C-2 of the phenyl ring.

Particularly useful insecticides of the present invention are the compounds of formula I having the preferred or notable structural features described above for the alcohols, and wherein R is the cyclopropanecarbonyl group of formula II. Insecticides of particular merit among this group are those wherein Y and Z are the same and each is a chlorine or bromine atom, preferably a chlorine atom, or one of Y and Z is a chlorine atom and the other is a trifluoromethyl group (see Table II). Especially active insecticides are those wherein R$^1$ is a methyl group and R$^2$ is a 2-thienyl group.

The insecticides of this invention having the acid residue of formula II have cis and trans isomeric forms; the carboxy and the substituted vinyl groups at the 1 and 3 positions of the cyclopropane ring are either cis or trans with respect to each other. Preparation of these compounds will usually yield a mixture of cis to trans isomers, designated cis,trans, in which the ratio of cis to trans may vary over a wide range. For purposes of this application the designation cis and trans are assigned in accordance with P. E. Burt, et al., *Pestic. Sci.*, 5 791–799 (1974). Certain compounds of this invention may also exist as E or Z isomers or as mixtures of E and Z isomers, designated E,Z, depending upon the spatial relationship of substituents on the α-carbon of the vinyl group to those on the β-carbon of the vinyl group.

In the cyclopropanecarboxylate art it is known there may be substantial differences in the level of insecticidal activity of the cis and trans isomers. In general, as between the cis and trans isomers of a given cyclopropanecarboxylate, the cis isomer is usually the more active, is also more active than the cis,trans mixture. Similar differences in activity may also occur with respect to the E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, the individual E and Z isomers, as well as the mixtures, are contemplated by and within the scope of the invention. The various enantiomers of the claimed compounds and mixtures of them are also included within the scope of the invention.

The novel insecticidal esters of this invention may be prepared by various methods which are exemplified below for the esters wherein R is the cyclopropanecarbonyl group of formula II.

Method A

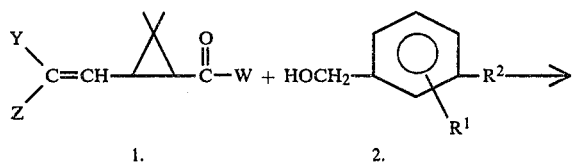

Method B

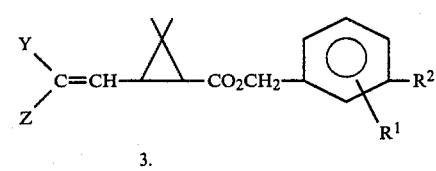

Method C

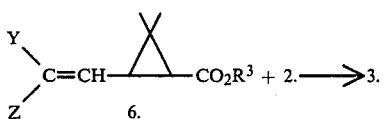

Method A is a normal esterification procedure. In this method the appropriate carboxylic acid is converted into an activated derivative for esterification, generally the carboxylic acid bromide or chloride, which is then allowed to react under anhydrous conditions with the alcohol 2.

Method B is an inverse esterification procedure wherein the carboxy oxygen of the appropriate acid, present as a salt, for example, the sodium, potassium, or ammonium salt, displaces a leaving group X from the alcohol derivative 5 to give the ester. Generally, X may be any good leaving group, but is preferably a bromine or chlorine atom or an alkyl- or arylsulfonyl group, particularly a bromine atom. This method offers a suitable alternative to Method A where an appropriate alcohol derivative is more accessible than the alcohol itself. The reaction of the salt of the acid with the alcohol derivative is preferably conducted under anhydrous conditions.

Method C involves a transesterification procedure. In this method the desired alcohol 2 exchanges with the existing alcohol moiety of an appropriate carboxylate to give the ester of the desired alcohol. The reaction is driven to completion by removal by distillation of the alcohol formed from the displaced alcohol moiety. Thus, to facilitate the transesterification, the undesired exchanged alcohol should have a boiling point lower than that of the desired alcohol. The reaction is catalyzed by either acids or bases. Particularly desirable catalysts are the titanium alcoholates, for example, titanium isopropoxide.

The intermediate acids from which the insecticidal esters of this invention are prepared are well known, and may be prepared by methods in the literature of the art. For example, tetramethylcyclopropanecarboxylic acid and 1-(4-chlorophenyl)-2-methylpropyl-1-carboxylic acid may be prepared by the methods outlined in *Synthetic Pyrethroids*, ACS Symposium Series, No. 42, M. Elliott, Ed., American Chemical Society, Washington, D.C., 1977, chapter 4, FIG. 4, page 48 and accompanying text; dihaloethenylcyclopropanecarboxylic acids, acids having the acyl group of formula II wherein each of Y and Z is a halogen atom, may be prepared by the method of Elliott et al., U.S. Pat. No. 4,024,163; and perhaloalkylethenylcyclopropanecarboxylic acids, acids wherein one of Y and Z is halogen and the other is a perhaloalkyl group in the partial structure of formula II, may be prepared by the method disclosed by Engel in European Patent Applicaton No. 79100163.9, Publication No. 3336, published Aug. 8, 1979. The pertinent disclosures of the above three citations are incorporated herein by reference.

In addition to the novel alcohols described above, intermediates of this invention include the compounds of formula III:

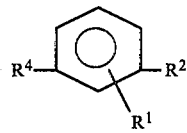

III wherein $R^1$ and $R^2$ are defined as above for the novel alcohols and insecticidal esters, and $R^4$ is methyl, bromomethyl, chloromethyl, bromo, chloro, formyl, 2-tetrahydropyranyloxymethyl, hydroxycarbonyl, cyano, or acetoxymethyl. The preferred position of the $R^1$ group on the phenyl ring is at C-2, between $R^4$ and $R^2$. Intermediates of particular merit are shown in Table III.

Other novel intermediates of this invention are 1-(3-thienyl)-3-methylcyclohexanol and 3-methyl-1-(3-thienyl)cyclohexene. These compounds are intermediates for the novel alcohol 3-(3-thienyl)phenylmethanol. Their utility is described in detail in Example 3. The cyclohexene compound is prepared by dehydration of the cyclohexanol, and is a mixture of the two possible isomers, the 1-cyclohexene and the 6-cyclohexene.

The following examples illustrate various methods of preparation for the novel alcohols and other intermediates of this invention. Methods for preparing the novel insecticidal esters are also shown. In the examples, all temperatures are in degrees Celsius, all pressures are in mm Hg, and reduced pressure for concentration of solvents was produced by a water aspirator unless otherwise specified.

EXAMPLE 1

Synthesis of 3-(2-thienyl)phenylmethyl cis-,trans-, and cis,trans-3-(2,2-dichloroethenyl)-2,2-dimethylcyclopropanecarboxylate (Method B)

Step 1: Preparation of 2-(3-bromomethylphenyl)thiophene (A) Preparation of 2-(3-methylphenyl)thiophene To a stirred solution of 107.0 g (1.0 mol) of m-toluidine and 185 mL of concentrated hydrochloric acid in 50 mL of water at 0° C. ±5° C. was added 75.9 g (1.1 mol) of sodium nitrite in 150 mL of water at such a rat as to maintain the reaction mixture temperature at 0° C. ±5° C. Upon complete addition, the reaction mixture was transferred to a Morton flask equipped with a mechanical stirrer, and 500 g (5.94 mol) of thiophene was added dropwise at 0° C. with stirring. A 1 molar aqueous solution of sodium hydroxide (275 mL) was then added, the reaction mixture temperature being maintained at 0° C. ±5° C. The reaction mixture was allowed to warm to ambient temperature and the resulting two phase mixture was separated. The aqueous phase was extracted with four portions of 300 mL each of toluene. The extracts were combined with the organic phase from above, and the whole was washed with two portions of a saturated aqueous solution of sodium chloride. The organic phase was dried with magnesium sulfate, filtered, and the filtrate concentrated under reduced pressure to give a dark residual oil. The residual oil was distilled under reduced pressure to give 31.4 g of crude product, b.p. 90°–108° C./0.075–0.35 mm. Purification by redistillation at 60° C./0.05 mm using a Kugelrohr distilling system, followed by column chromatography on silica gel using hexane as an eluent, gave 10.0 g of 2-(3-methylphenyl)thiophene.

The nmr spectrum was consistent with the proposed structure.

(B) Bromination of 2-(3-methylphenyl)thiophene

A stirred solution of 9.4 g (0.054 mol) of 2-(3-methylphenyl)thiophene and 9.6 g (0.054 mol) of N-bromosuccinimide in 275 mL of carbon tetrachloride was irradiated with white light for 4 hours at reflux temperature. The reaction mixture was stirred for 16 hours without external heating, then cooled in an ice-water bath for 15 minutes, and filtered. The filter cake was washed with two portions of 50 mL each of carbon tetrachloride, and the washes were combined with the filtrate, and the whole washed with 200 mL of a saturated aqueous solution of sodium chloride. The organic phase was dried with magnesium sulfate, filtered, and the filtrate concentrated under reduced pressure to give the product as a dark residual oil. The product was further purified by column chromatography on silica gel using hexane as an eluent. The appropriate fractions were combined to give 4.0 g of 2-(3-bromomethylphenyl)thiophene.

The nmr spectrum was consistent with the proposed structure.

Step 2: Reaction of 2-(3-bromomethylphenyl)thiophene with potassium cis,trans-3-(2,2-dichloroethenyl)-2,2-dimethylcyclopropanecarboxylate To a stirred homogeneous mixture of 1.0 g (0.016 mol) of potassium hydroxide and 6 mL of water was added 3.3 g (0.016 mol) of cis,trans-3-(2,2-dichloroethenyl)-2,2-dimethylcyclopropanecarboxylic acid. The mixture was warmed to 40° C. for 15 minutes, 100 mL of heptane was added, and the reaction mixture was heated under reflux and the water by-product collected in a Dean-Stark trap attached to the reaction vessel. Upon complete collection of water, 4.0 g (0.016 mol) of 2-(bromomethylphenyl)thiophene, 0.1 g of 1,4-diazabicyclo[2.2.2]octane, and 60 mL of acetonitrile were added. The reaction mixture was heated under reflux for 1.5 hours, then transferred to a separatory funnel containing 100 g of ice. The reaction vessel was washed with 50 mL of water and 50 mL of acetonitrile, and the washes added to the reaction mixture in the separatory funnel. The mixture was extracted with four portions of 75 mL each of heptane. The combined heptane extracts were dried with magnesium sulfate, filtered, and the filtrate concentrated under reduced pressure to give a residual oil. The residual oil was distilled under reduced pressure using a Kugelrohr distilling system. A cut from the distillation boiling at 165° C. ±2° C./0.08 mm was determined by nmr and ir analysis to be 3-(2-thienyl)phenylmethyl cis,trans-3-(2,2-dichloroethenyl)-2,2-dimethylcyclopropanecarboxylate. The yield was 0.75 g.

Analysis calc'd for $C_{19}H_{18}Cl_2O_2S$: C 59.85; H 4.74; Found: C 59.68; H 4.90.

Cuts from the distillation boiling at 165° C.±2° C./0.08 mm and 150°–160° C./0.08 mm were combined and subjected to column chromatography on silica gel, eluting with hexane:ethyl acetate (50:1). The appropriate fractions were combined and subjected to medium pressure liquid chromatography using hexane:ethyl acetate (50:1). The appropriate fractions were combined and distilled under reduced pressure using a Kugelrohr distilling system to give 0.84 g of 3-(2-thienyl)phenylmethyl cis-3-(2,2-dichloroethenyl)-2,2-dimethylcyclopropanecarboxylate, b.p. 168° C.±2° C./0.10 mm.

The nmr and the ir spectra were consistent with the proposed structure.

Other fractions from the medium pressure liquid chromatography were combined to give 0.76 g of 3-(2-thienyl)phenylmethyl trans-3-(2,2-dichloroethenyl)-2,2-dimethylcyclopropanecarboxylate.

The nmr spectum was consistent with the proposed structure.

EXAMPLE 2

Synthesis of 3-(3-thienyl)phenylmethyl cis-3-(2,2-dichloroethenyl)-2,2-dimethylcyclopropanecarboxylate (Method A)

Step 1: Preparation of 3-(3-thienyl)phenylmethanol (A) Preparation of 1-(3-thienyl)-3-methylcyclohexanol A stirred solution of 36.3 g (0.223 mol) of 3-bromothiophene in 50 mL of dry tetrahydrofuran was cooled to −78° C. in a dry ice-acetone bath. To this solution was added dropwise 139.4 mL (14.3 g, 0.223 mol, 1.6 M in hexane) of n-butyllithium in hexane over 30 minutes. Upon complete addition, the reaction mixture was stirred at −78° C. for 1.5 hours, then 25.0 g 0.223 mol, of 3-methylcyclohexanone was added dropwise during 20 minutes. Upon complete addition, the reaction mixture was stirred at −78° C. for two hours. The cooling bath was removed, and the reaction mixture was allowed to warm to ambient temperature during 1.5 hours, then was stirred for an additional one hour. Diethyl ether saturated with water (50 mL) was added with stirring, and the mixture was poured into a mixture of 50 g of ice and 20 mL of concentrated hydrochloric acid. The layers were separated, and the aqueous layer was washed with two portions of 200 mL each of diethyl ether. The washings were combined with the organic layer, and the whole was washed with 300 mL of a saturated aqueous solution of sodium chloride. The organic layer was dried with magnesium sulfate, filtered, and the filtrate concentrated under reduced pressure to give 44.0 g of 1-(3-thienyl)-3-methylcyclohexanol. Volatile components were removed from the product by distillation at 50° C./0.25 mm using a Kugelrohr distilling system.

(B) Preparation of 3-methyl-1-(3-thienyl)cyclohexene

A stirred solution of 37.6 g (0.192 mol) of 1-(3-thienyl)-3-methylcyclohexanol and 0.5 g of p-toluenesulfonic acid in 200 mL of toluene was heated under reflux, and by-product water was collected in a Dean-Stark trap attached to the reaction vessel. After about 16.5 hours, the reaction mixture was cooled and concentrated under reduced pressure to give a residual oil. The oil was subjected to distillation under reduced pressure using a Kugelrohr distilling system to give 11.6 g of 3-methyl-1-(3-thienyl)cyclohexene b.p. 105° C.±5° C./0.25 mm.

The nmr and ir spectra were consistent with the proposed structure.

(C) Preparation of 3-(3-methylphenyl)thiophene

A stirred solution of 11.6 g (0.065 mol) of 3-metyhyl-1-(3-thienyl)cyclohexene and 32.0 g (0.130 mol) of tetrachloro-o-benzoquinone in 100 mL of dry toluene was heated under reflux, and by-product water was collected in a Dean-Stark trap attached to the reaction vessel. After about 24 hours, the reaction mixture was cooled, a solid removed by filtration, and the filtrate concentrated under reduced pressure to give a black residual oil. The collected solid was digested with 450 mL of hexane with stirring for 0.5 hour. The mixture was cooled and filtered, and the filtrate concentrated under reduced pressure to give a small amount of an oily solid which was dissolved in 20 mL of hexane. The hexane solution was filtered, and the filtrate concentrated to give a dark residual oil. This oil was combined with the black residual oil from above, and the whole was subjected to column chromatography on silica gel, eluting with hexane. The appropriate fractions were combined to give 9.8 g of 3-(3-methylphenyl)thiophene.

The nmr and ir spectra were consistent with the proposed structure.

(D) Preparation of 3-(3-bromomethylphenyl)thiophene

A stirred solution of 9.8 g (0.056 mol) of 3-(3-methylphenyl)thiophene in 250 mL of carbon tetrachloride was heated to reflux, and 0.5 g of benzoyl peroxide was added. Heating was continued, and after five minutes an additional 0.5 g of benzoyl peroxide and 10 g of N-bromosuccinimide were added. Upon complete addition, the reaction mixture was heated under reflux for an additional 2.5 hours, then cooled in an ice-water bath for one hour. The reaction mixture was filtered, and the filter cake washed with 50 mL of carbon tetrachloride. The wash and filtrate were combined, and the whole was washed with 200 mL of a saturated aqueous solution of sodium chloride. The organic layer was dried with magnesium sulfate, filtered, and the filtrate concentrated under reduced pressure to give a residual oil. The residual oil was subjected to distillation under reduced pressure using a Kugelrohr distilling system to give 8.7 g of 3-(3-bromomethylphenyl)thiophene, b.p. 95°–150° C./0.1 mm.

The nmr and ir spectra were consistent with the proposed structure.

(E) Preparation of 3-(3-thienyl)phenylmethyl acetate

A stirred solution of 8.7 g (0.034 mol) of 3-(3-bromomethylphenyl)thiophene and 5.1 g (0.051 mol) of potassium acetate in 65 mL of glacial acetic acid was heated under reflux for three hours. The reaction mixture was cooled and transferred to a separatory funnel, and 150 mL of water was added. The mixture was extracted with two portions of 120 mL each of methylene chloride. The combined extracts were washed with 150 mL of a saturated solution of sodium chloride, two portions of 150 mL each of a saturated aqueous solution of sodium bicarbonate, and finally 100 mL of a saturated aqueous solution of sodium chloride. The organic layer was dried with magnesium sulfate, filtered, and the filtrate concentrated under reduced pressure to give an oil residue. The residue was subjected to column chromatography on silica gel, eluting with hexane:methylene chloride (3:2). The appropriate fractions were combined to give 3.3 g of 3-(3-thienyl)phenylmethyl acetate.

The nmr and ir spectra were consistent with the proposed structure.

(F) Hydrolysis of 3-(3-thienyl)phenylmethyl acetate

To 3.3 g (0.014 mol) of 3-(3-thienyl)phenylmethyl acetate was added with stirring a solution of 1.4 g (0.021 mol) of potassium hydroxide in 100 mL of methanol. The reaction mixture was stirred at ambient temperature for 19 hours. The volume of the reaction mixture was reduced to to 30 mL by concentration under reduced pressure. The concentrate was placed in a separatory funnel, and 100 mL of a saturated aqueous solution of sodium chloride was added. The mixture was extracted with five portions of 60 mL each of methylene chloride. The extracts were combined and washed with 200 mL of a saturated aqueous solution of sodium chloride. The organic layer was dried with magnesium sulfate, filtered, and the filtrate concentrated under reduced pressure to give a residual oil. The oil was subjected to column chromatography on silica gel, eluting with toluene:pentane (3:2). The appropriate fractions were combined to give 2.8 g of 3-(3-thienyl)phenylmethanol.

The nmr and ir spectra were consistent with the proposed structure.

Step 2: Reaction of 3-(3-thienyl)phenylmethanol with cis-3-(2,2-dichloroethyl)-2,2-dimethylcyclopropanecarbonyl chloride To a stirred solution of 1.0 g (0.005 mol) of 3-(3-thienyl)phenylmethanol and 0.5 g (0.005 mol) of pyridine in 25 mL of methylene chloride was added in one portion 1.2 g (0.005 mol) of cis-3-(2,2-dichloroethenyl)-2,2-dimethylcyclopropanecarbonyl chloride in 5 mL of methylene chloride. The reaction mixture was stirred at ambient temperature for 17 hours, then transferred to a separatory funnel, and diluted with 200 mL of methylene chloride. The solution was washed with 200 mL of aqueous 2 N hydrochloric acid, 200 mL of a saturated aqueous solution of sodium chloride, 200 mL of a cold aqueous 2 N solution of sodium hydroxide, and finally, 200 mL of a saturated aqueous solution of sodium chloride. The organic layer was dried with magnesium sulfate, filtered, and the filtrate concentrated under reduced pressure to give a residual oil. The oil was subjected to medium pressure liquid chromatography using petroleum ether:ethyl acetate (55:1) as the eluent. The appropriate fractions were combined and subjected to distillation under reduced pressure using a Kugelrohr distilling system to give 0.1 g of 3-(3-thienyl)-phenylmethyl cis-3-(2,2-dichloroetheny)-2,2-dimethylcyclopropanecarboxylate.

The nmr and ir spectra were consistent with the proposed structure.

EXAMPLE 3

Synthesis of [2-methyl-3-(2-thienyl)phenyl]-methyl cis-3-(2-chloro-3,3,3-trifluoro-1-propenyl)-2,2-dimethylcyclopropanecarboxylate (Method A)

Step 1: Preparation of 2-methyl-3-(2-thienyl)phenylmethanol (A) Preparation of 2-(3-chloro-2-methylphenyl)thiophene To a stirred solution of 50.0 g (0.353 mol) of 3-chloro-2-methylaniline in 100 g (1.19 mol) of thiophene was added dropwise 82.7 g (0.706 mol) of isoamyl nitrite during 0.5 hour. Upon complete addition, the reaction mixture was heated to reflux temperature, and stirred for 0.75 hour. The reaction mixture was then allowed to cool to ambient temperature, and stirring was continued for 16 hours. The reaction mixture was concentrated under reduced pressure to give a black residual oil. The oil was subjected to column chromatography on silica gel, eluting with heptane, then heptane:ethyl acetate (40:1). The appropriate fractions were combined to give a red oil which was subjected to distillation under reduced pressure using a Kugelrohr distilling system to give 9.2 g of 2-(3-chloro-2methylphenyl)thiophene, b.p. 78° C.±3° C./0.05 mm.

The nmr and ir spectra were consistent with the proposed structure.

Analysis calc'd for $C_{11}H_{19}ClS$: C 63.31; H 4.34; Found: C 63.01; H 4.61.

(B) Preparation of 2-methyl-3-(2-thienyl)benzoic acid

To a flame-dried reaction vessel were added 2.5 g (0.103 mol) of magnesium turnings and 20 mL of tetrahydrofuran, and the mixture was stirred. A solution of 21.5 g (0.103 mol) of 2-(3-chloro-2-methylphenyl)thiophene is 20 mL of tetrahydrofuran, followed by an additional 50 mL of tetrahydrofuran, were added, and the reaction mixture was heated under reflux for 18 hours, then cooled to −78° C. An additional 100 mL of tetrahydrofuran, followed by 50 mL of tetrahydrofuran saturated with carbon dioxide, were added. Upon complete addition, gaseous carbon dioxide was bubbled into the reaction mixture until ambient temperature was reached. The reaction mixture was filtered, and the filtrate concentrated under reduced pressure to give a residue. The residue was dissolved in 300 mL of methylene chloride. An attempt to extract the methylene chloride solution with an aqueous 2 N solution of sodium hydroxide resulted in the formation of an emulsion. The emulsion was made acidic by the addition of concentrated hydrochloric acid, and was then extracted with three portions of 300 mL each of methylene chloride. The combined extracts were washed with four portions of 200 mL each of an aqueous 2 N solution of sodium hydroxide.

The basic washes were combined, acidified with concentrated hydrochloric acid, and extracted with four portions of 200 mL each of methylene chloride. The organic phases were combined, dried with magnesium sulfate, filtered, and the filtrate concentrated under reduced pressure to give a residual oil. The oil was subjected to column chromatography on silica gel, eluting with methylene chloride. The appropriate fractions were combined, and the solvent removed under reduced pressure to give a residual oil which was dissolved in 125 mL of a saturated aqueous solution of sodium bicarbonate. The solution was extracted with two portions of 100 mL each of methylene chloride. The aqueous layer was cautiously acidified with concentrated hydrochloric acid, and extracted with three portions of 100 mL each of methylene chloride. The three methylene chloride extracts were combined, dried with magnesium sulfate, filtered, and the filtrate concentrated under reduced pressure to give a residual solid. Recrystallization from heptane:toluene (9:1) gave 6.9 g of 2-methyl-3-(2-thienyl)-benzoic acid, m.p. 91.5°–93° C.

The nmr and ir spectra were consistent with the proposed structure.

Analysis calc'd for $C_{12}H_{10}O_2S$: C 66.04; H 4.61; Found: C 65.88; H 4.83.

(C) Reduction of 2-methyl-3-(2-thienyl)benzoic acid

Under an argon atmosphere, a stirred solution of 5.7 g (0.026 mol) of 2-methyl-3-(2-thienyl)benzoic acid in 50 mL of tetrahydrofuran was cooled to 0° C.±2° C. To this solution was added dropwise 4.4 g (0.051 mol, 51.3 mL of a 1.0 M solution) of borane tetrahydrofuran complex. The addition was made over 35 minutes. The reaction mixture was stirred for 0.5 hour at ambient temperature, then for two hours at reflux temperature. The reaction mixture was cooled, and 100 mL of diethyl ether saturated with water, then 20 mL of water, were cautiously added. The mixture was transferred to a separatory funnel containing 50 mL of ice, and was saturated with solid sodium chloride, and extracted with three portions of 200 mL each of diethyl ether. The combined extracts were dried with magnesium sulfate, filtered, and the filtrate concentrated under reduced pressure to give 5.3 g of 2-methyl-3-(2-thienyl)-phenylmethanol as an oil.

The nmr and ir spectra were consistent with the proposed structure.

Step 2: Reaction of 2-methyl-3-(2-thienyl)phenylmethanol with cis-3-(2-chloro-3,3,3-trifluoro-1-propenyl)-2,2-dimethylcyclopropanecarbonyl chloride A stirred solution of 1.35 g (0.007 mol) of 2-methyl-3-(2-thienyl)phenylmethanol and 0.55 g (0.007 mol) of pyridine in 30 mL of toluene was warmed to 45° C., and a solution of 1.7 g (0.007 mol) of cis-3-(2-chloro-3,3,3-trifluoro-1-propenyl)-2,2-dimethylcyclopropanecrbonyl chloride in 3 mL of toluene was added. Upon complete addition, the reaction mixture was heated at 53° C. for 0.5 hour, then allowed to cool to ambient temperature, and stirred for 16 hours. The reaction mixture was transferred to a separatory funnel, and diluted with 400 mL of n-heptane. The solution was washed with 200 mL of an aqueous 2 N solution of hydrochloric acid, then with 200 mL of an aqueous 2 N solution of sodium hydroxide. The organic layer was dried with magnesium sulfate, filtered, and the filtrate concentrated under reduced pressure to give a residual oil. The oil was distilled under reduced pressure using a Kugelrohr distilling system to give 2.19 g of [2-methyl-3-(2-thienyl)-phenyl]methyl cis-3-(2-chloro-3,3,3-trifluoro-1-propenyl)-2,2-dimethylcyclopropanecarboxylate, b.p. 140° C./0.05 mm.

The nmr and ir spectra were consistent with the proposed structure.

Analysis calc'd for $C_{21}H_{20}ClF_3O_2S$: C 58.81; H 4.70; Found: C 58.48; H 4.74.

EXAMPLE 4

Synthesis of [2-methyl-3-(2-thienyl)phenyl]-methyl trans-3-(2,2-dichloroethenyl)-2,2-dimethylcyclopropanecarboxylate (Method A)

This compound was prepared in the manner of Example 3, Step 2 using 0.70 g (0.003 mol) of trans-3-(2,2-dichloroethenyl)-2,2-dimethylcyclopropanecarbonyl chloride, 0.63 g (0.003 mol) of 2-methyl-3-(2-thienyl)-phenylmethanol (prepared in the manner of Example 3, Step 1), and 0.30 g (0.004 mol) of pyridine in 20 mL of toluene. The yield of [2-methyl-3-(2-thienyl)phenyl]-methyl trans-3-(2,2-dichloroethenyl)-2,2-dimethylcyclopropanecarboxylate was 0.44 g, b.p. 165° C./0.05 mm.

The nmr and ir spectra were consistent with the proposed structure.

Analysis calc'd for $C_{20}H_{20}Cl_2O_2S$: C 60.76; H 5.09; Found: C 59.13; H 4.62.

EXAMPLE 5

Synthesis of [2-methyl-3-(2-thienyl)phenyl]-methyl cis-3-(2,2-dichloroethenyl)-2,2-dimethylcyclopropanecarboxylate (Method A)

This compound was prepared in the manner of Example 3, Step 2 using 1.50 g (0.007 mol) of cis-3-(2,2-dichloroethenyl)-2,2-dimethylcyclopropanecarbonyl chloride, 1.35 g (0.007 mol) of 2-methyl-3-(2-thienyl)-phenylmethanol (prepared in the manner of Example 3, Step 1), and 0.52 g (0.007 mol) of pyridine in 30 mL of toluene. The yield of [2-methyl-3-(2-thienyl)phenyl]-methyl cis-3-(2,2-dichloroethenyl)-2,2-dimethylcyclopropanecarboxylate was 2.0 g, b.p. 160° C./0.05 mm.

The nmr and ir spectra were consistent with the proposed structure.

Analysis calc'd for $C_{20}H_{20}Cl_2O_2S$: C 60.76; H 5.09; Found: C 60.84; H 5.75.

EXAMPLE 6

Synthesis of [2-methyl-3-(2-thienyl)phenyl]-methyl 1R-cis-3-(2,2-dichloroethenyl)-2,2-dimethylcyclopropanecarboxylate (Method A)

This compound was prepared in the manner of Example 3, Step 2 using 1.10 g (0.005 mol) of 2-methyl-3-(2-thienyl)-phenylmethanol (prepared in the manner of Example 3, Step 1), 0.42 g (0.005 mol) of pyridine, 33 mL of toluene, and 1.20 g (0.005 mol) of 1R-cis-3-(2,2-dichloroethenyl)-2,2-dimethylcyclopropanecarbonyl chloride. The crude oily product was subjected to column chromatography on silica gel, eluting with heptane:ethyl acetate (30:1). The appropriate fractions were combined to give 1.78 g of [2-methyl-3-(2-thienyl)phenyl]-methyl 1R-cis-3-(2,2-dichloroethenyl)-2,2-dimethylcyclopropanecarboxylate.

The nmr and ir spectra were consistent with the proposed structure.

Analysis calc'd for $C_{20}H_{20}Cl_2O_2S$: C 60.76; H 5.09; Found: C 61.30; H 5.50.

EXAMPLE 7

Synthesis of [2-methyl-3-(2-thienyl)phenyl]-methyl cis-3-(2,2-dibromoethenyl)-2,2-dimethylcyclopropanecarboxylate (Method A)

This compound was prepared in the manner of Example 3, Step 2 using 1.70 g (0.054 mol) of cis-3-(2,2-dibromoethenyl)-2,2-dimethylcyclopropanecarbonyl chloride, 1.10 g (0.054 mol) of 2-methyl-3-(2-thienyl)-phenylmethanol (prepared in the manner of Example 3, Step 1) and 0.42 g of pyridine in 30 mL of toluene. The yield of [2-methyl-3-(2-thienyl)phenyl]-methyl cis-3-(2,2-dibromoethenyl)-2,2-dimethylcyclopropanecarboxylate was 1.97 g.

The nmr and ir spectra were consistent with the proposed structure.

Analysis calc'd for $C_{20}H_{20}Br_2O_2S$: C 49.61; H 4.16; Found: C 49.79; H 4.34.

EXAMPLE 8

Synthesis of [3-(5-Bromofuranyl)phenyl]-methyl cis-3-(2,2-dichloroethenyl)-2,2-dimethylcyclopropanecarboxylate (Method A)

Step 1: Preparation of 3-(2-Bromo-5-furanyl)phenylmethanol (A) Preparation of 2-(3-methylphenyl)furan Under a dry nitrogen atmosphere, a solution of 50.0 g (0.467 mol) of m-toluidine in 1 L of furan was prepared. To this solution 93.7 g (0.800 mol) of isoamyl nitrite was added dropwise with stirring during 30 minutes. Upon complete addition, the reaction mixture was heated to reflux, and was stirred for 18 hours. The excess furan and isoamyl nitrite were then removed by distillation under reduced pressure to give a residue. The residue was dissolved in chloroform, and washed with 200 mL of a saturated aqueous solution of sodium chloride. The organic layer was dried with sodium sulfate, filtered, and the filtrate concentrated under reduced pressure to give a residual oil. The oil was subjected to column chromatography on silica gel, eluting with hexane, then with toluene:hexane (1:1). Appropriate fractions containing impure product were combined and subjected to distillation under reduced pressure using a Kugelrohr distilling system. The fraction boiling at 50°–62° C./0.2 mm was combined with fractions from the chromatography which contained essentially pure product. The combination was filtered through activated carbon, and subjected to column chromatography on silica gel, eluting with hexane. The appropriate fractions were combined to give 23.2 g of 2-(3-methylphenyl)furan.

The ir spectrum was consistent with the proposed structure.

(B) Preparation of 2-Bromo-5-(3-methylphenyl)-furan

A stirred solution of 10.0 g (0.063 mol) of 2-(3-methylphenyl)furan in 250 mL of carbon tetrachloride was heated to reflux, and 0.1 g of benzoyl peroxide was added. The solution was heated at reflux for ten minutes, then an additional 0.1 g of benzoyl peroxide followed by 11.2 g (0.063 mol) of N-bromosuccinimide, were added. Upon complete addition, refluxing was continued for an additional 18 hours. The reaction mixture was cooled, filtered, and the filtrate washed with 200 mL of a saturated aqueous solution of sodium chloride. The organic layer was dried with magnesium sulfate, filtered, and the filtrate concentrated under reduced pressure to give 13.7 g of 2-bromo-5-(3-methylphenyl)furan.

The nmr and ir spectra were consistent with the structure.

(C) Preparation of 2-Bromo-5-(3-bromomethylphenyl)-furan

This compound was prepared in the manner of Step 1B above using 6.9 g (0.029 mol) of 2-bromo-5-(3- methylphenyl)furan, 5.2 g (0.025 mol) of N-bromosuccinimide, and 0.2 g of benzoyl peroxide in 125 mL of carbon tetrachloride. The yield of 2-bromo-5-(3-bromomethylphenyl)furan was 7.4 g.

The nmr and ir spectra were consistent with the proposed structure.

(D) Preparation of 3-(2-Bromo-5-furanyl)phenylmethyl acetate

A stirred solution of 7.3 g (0.023 mol) of 2-bromo-5-(3-bromomethylphenyl)furan in 50 mL of acetic acid was cooled in an ice-water bath, and 3.4 g (0.035 mol) of potassium acetate was added. Upon complete addition, the reaction mixture was heated to reflux temperature and stirred for 19 hours. The reaction mixture was transferred to a separatory funnel, diluted with 100 mL of water, then extracted with two portions of 150 mL each of chloroform. The combined extracts were washed with one portion of 150 mL of a saturated aqueous solution of sodium chloride, two portions of 150 mL each of a saturated aqueous solution of sodium bicarbonate, and finally with one portion of 200 mL of a saturated aqueous solution of sodium chloride. The organic layer was dried with magnesium sulfate, filtered, and the filtrate concentrated under reduced pressure to give a residual oil. The oil was subjected to column chromatography on silica gel, eluting with hexane: chloroform (2:1). The appropriate fractions were combined to give 3.8 g of 3-(2-bromo-5-furanyl)phenylmethyl acetate.

The nmr and ir spectra were consistent with the proposed structure.

(E) Hydrolysis of 3-(2-bromo-5-furanyl)phenylmethyl acetate

A solution of 3.8 g (0.013 mol) of 3-(2-bromo-5-furanyl)-phenylmethyl acetate and 0.85 g (0.019 mol) of potassium hydroxide in 100 mL of methanol was stirred for 75 minutes at ambient temperature. The reaction mixture was diluted with 200 mL of water, saturated with solid sodium chloride, and extracted with three portions of 150 mL each of chloroform. The combined extracts were dried with magnesium sulfate, filtered, and the filtrate concentrated under reduced pressure to give 2.9 g of 3-(2-bromo-5-furanyl)phenylmethanol.

The nmr and ir spectra were consistent with the proposed structure.

Step 2: Esterification of cis-3-(2,2-dichloroethenyl)-2,2-dimethylcyclopropanecarboxylic acid with 3-(2-bromo-5-furanyl)phenylmethanol Under a dry nitrogen atmosphere, a stirred solution of 1.2 g (0.006 mol) of cis-3-(2,2-dichloroethenyl)-2,2-dimethylcyclopropanecarboxylic acid in 40 mL of toluene was heated to 80° C.±5° C. To this solution was added a solution of 0.7 g (0.006 mol) of oxalyl chloride in 5 mL of toluene. Upon complete addition, the reaction mixture was heated at 82° C.±5° C. for 60 hours. The reaction mixture was cooled to ambient temperature, and 0.9 g (0.011 mol) of pyridine was added. The reaction mixture was stirred for two hours, then warmed to 70° and 1.4 g (0.006 mol) of 3-(2-bromo-5-furanyl)phenylmethanol in 10 mL of toluene was added. Upon complete addition, the reaction mixture was stirred at 70° C.±5° C. for 21.5 hours. The reaction mixture was transferred to a separatory funnel, 200 mL of toluene washings were added, and the mixture was washed with 100 mL of an aqueous 2 N hydrochloric acid solution, 100 mL of a saturated aqueous solution of sodium chloride, 100 mL of an aqueous 2 N solution of sodium hydroxide, and finally 100 mL of a saturated aqueous solution of sodium chloride. The organic layer was dried with magnesium sulfate, filtered, and the filtrate concentrated under reduced pressure to give a residual oil. The oil was subjected to medium pressure liquid chromatography using hexane:ethyl acetate (46:1). The appropriate fractions were combined and concentrated to give a crystalline solid. The solid was recrystallized from methanol, then from hexane to give 0.9 g of [3-(5-bromofuranyl)phenyl]methyl cis-3-(2,2-dichloroethenyl)-2,2-dimethylcyclopropanecarboxylate, m.p. 76.5°–77° C.

The nmr and ir spectra were consistent with the proposed structure.

Analysis calc'd for $C_{19}H_{17}BrCl_2O_3$: C 51.38; C 3.86; Found: C 51.88; C 4.20.

EXAMPLE 9

Synthesis of [3-(2-Furanyl)phenyl]methyl cis-3-(2,2-dichloroethenyl)-2,2-dimethylcyclopropanecarboxylate (Method A)

Step 1: Preparation of 3-(2-Furanyl)phenylmethanol (A) Preparation of 2-(3-Bromophenyl)furan This compound was prepared in the manner of Example 8, Step 1A using 50.0 g (0.241 mol) of m-bromoaniline and 68.0 g (0.581 mol) of isoamyl nitrite in 234 g (3.44 mol) of furan. The yield of 2-(3-bromophenyl)furan was 32.9 g.

The nmr and ir spectra were consistent with the proposed structure.

Analysis calc'd for $C_{10}H_7BrO$: C 53.84; H 3.16; Found: C 53.67; H 3.45.

(B) Preparation of 3-(2-Furanyl)benzaldehyde

Under a nitrogen atmosphere a stirred solution of 15.0 g (0.067 mol) of 2-(3-bromophenyl)furan in 50 mL of diethyl ether and 60 mL of dry tetrahydrofuran was cooled to −72° C.±5° C. To this solution was added dropwise 4.3 g (0.067 mol) of n-butyllithium (42 mL, 1.6 M in hexane) during 30 minutes. A stirred solution of 5.4 g (0.074 mol) of dimethylformamide in 50 mL of diethyl ether and 60 mL of dry tetrahydrofuran in a Morton flask was cooled under a dry nitrogen atmosphere to −70° C.±5° C. Using a flexible needle tube, the solution of the 2-(3-lithiumphenyl)furan intermediate formed above was transferred by pressure differential to the dimethylformamide solution. Upon complete addition, the reaction mixture was allowed to warm to ambient temperature during 2 hours, then transferred to a separatory funnel with the aid of 150 mL of ice-water. The mixture was saturated with solid sodium chloride, and extracted with two portions of 200 mL each of diethyl ether. The combined extracts were dried with magnesium sulfate, filtered, and the filtrate concentrated under reduced pressure to give a residual oil. A solution of the oil in 30 mL of absolute ethanol was added to a Morton flask containing 150 mL of a saturated aqueous solution of sodium metabisulfite. The reaction mixture was stirred for 16 hours, and a solid which had formed was collected on a filter paper, and washed with methyl ethyl ketone-diethyl ether (3:7), methyl ethyl ketone-diethyl ether (2:8), methyl ethyl ketone-diethyl ether (1:9), and two portions of diethyl ether. The solid was dissolved in water, and the solution made basic with a saturated aqueous solution of sodium bicarbonate. The mixture was extracted with four portions of 100 mL each of methylene chloride. The combined extracts were dried with magnesium sulfate, filtered, and the filtrate concentrated under reduced pressure to give 4.7 g of a residual oil. The methyl ethyl ketone-diethyl ether washes from above were combined, diluted with 200 mL of diethyl ether, and extracted with 100 mL of water. The aqueous phase was made basic by the addition of a saturated aqueous solution of sodium bicarbonate. The basic mixture was extracted with four portions of 100 mL each of methylene chloride. The combined methylene chloride extracts were dried with magnesium sulfate, filtered, and the filtrate concentrated under reduced pressure to give 1.0 g of residual oil which was combined with the 4.7 g of oil obtained above. The oil was subjected to distillation under reduced pressure using a Kugelrohr distilling system to give 3.0 g of 3-(2-furanyl)benzaldehyde, b.p. 83° C.±1° C./0.1 mm.

The nmr and ir spectra were consistent with the proposed structure.

(C) Reduction of 3-(2-furanyl)benzaldehyde

A solution of 3.0 g (0.017 mol) of 3-(2-furanyl)benzaldehyde and 0.66 g (0.017 mol) of sodium borohydride in 30 mL of ethanol was stirred at ambient temperature for 18 hours. The reaction mixture was concentrated under reduced pressure to give a residual oil. The oil was dissolved in a mixture of methylene chloride and water, and was saturated with solid sodium chloride, then extracted with three portions of 100 mL each of methylene chloride. The combined extracts were dried with magnesium sulfate, filtered, and the filtrate concentrated under reduced pressure to give 3.0 g of 3-(2-furanyl)-phenylmethanol.

The nmr and ir spectra were consistent with the proposed structure.

Step 2: Reaction of 3-(2-furanyl)phenylmethanol with cis-3-(2,2-dichloroethenyl)-2,2-dimethylcyclopropanecarbonyl chloride This reaction was conducted in the manner of Example 3, Step 2 using 1.5 g (0.009 mol) of 3-(2-furanyl)-phenylmethanol, 0.7 g (0.009 mol) of pyridine, 50 mL of toluene, and 2.0 g (0.009 mol) of cis-3-(2,2-dichloroethenyl)-2,2-dimethylcyclopropanecarbonyl chloride. The crude oily product was subjected to distillation under reduced pressure to give 3.1 g of [3-(2-furanyl)-phenyl]methyl cis-3-(2,2-dichloroethenyl)-2,2-dimethylcyclopropanecarboxylate, b.p. 160° C./0.1 mm.

The nmr and ir spectra were consistent with the proposed structure.

Analysis calc'd for $C_{19}H_{18}Cl_2O_3$: C 62.48; H 4.96; Found: C 61.29; H 4.95.

EXAMPLE 10

Synthesis of [3-(2-furanyl)phenyl]methyl cis-3-(2-chloro-3,3,3-trifluoro-1-propenyl)-2,2-dimethylcyclopropanecarboxylate (Method A)

This compound was prepared in the manner of Example 3, Step 2 using 2.3 g (0.008 mol) of cis-3-(2-chloro-3,3,3-trifluoro-1-propenyl)-2,2-dimethylcyclopropanecarbonyl chloride, 1.5 g (0.008 mol) of 3-(2-furanyl)phenylmethanol, 0.7 g (0.008 mol) of pyridine, and 50 mL of toluene. The yield of [3-(2-furanyl)-phenyl]methyl cis-3-(2-chloro-3,3,3-trifluoro-1-propenyl)-2,2-dimethylcyclopropanecarboxylate was 2.5 g, b.p. 129° C.±3° C./0.1 mm.

The nmr and ir spectra were consistent with the proposed structure.

Analysis calc'd for $C_{20}H_{18}ClF_3O_3$: C 60.24; H 4.55; Found: C 60.13; H 4.79.

EXAMPLE 11

Synthesis of [3-(2-furanyl)-2-methylphenyl]methyl cis-3-(2-chloro-3,3,3-trifluoro-1-propenyl)-2,2-dimethylcyclopropanecarboxylate (Method A)

Step 1: Preparation of 3-(2-furanyl)-2-methylphenylmethanol (A) Preparation of 2-methyl-3-nitrophenylmethyl acetate To 600 mL of toluene in a Morton reaction flask was added 100 g (0.598 mol) of 2-methyl-3-nitrophenylmethanol with stirring. The solution was heated to reflux, and 100 mL of toluene was removed by distillation into a Dean Stark trap. The solution was cooled, and 48.3 mL of pyridine was added. After further cooling with an ice-water bath, 51.6 g (0.658 mol) of acetyl chloride was added dropwise. Upon complete addition, the reaction mixture was allowed to warm to ambient temperature, and was stirred for 16 hours. The reaction mixture was heated under reflux for 3.5 hours, cooled to ambient temperature, then poured over 1 L of ice. When the ice had melted, the organic layer was separated, and the aqueous layer washed with three portions of 300 mL each of toluene. The toluene wash was combined with the organic layer, and the whole was washed with two portions of 250 mL each of aqueous 2 N hydrochloric acid, 250 mL of saturated aqueous solution of sodium chloride, two portions of 250 mL each of an aqueous 2 N solution of sodium hydroxide, and finally, 250 mL of a saturated aqueous solution of sodium chloride. The organic layer was dried with magnesium sulfate, filtered, and the filtrate concentrated under reduced pressure to give a residual oil. The oil was subjected to distillation using a Kugelrohr distilling system to give 107.3 g of 2-methyl-3-nitrophenylmethyl acetate, b.p. 120° C./0.25 mm.

The ir spectrum was consistent with the proposed structure.

(B) Preparation of 3-amino-2-methylphenylmethyl acetate

Using a Parr hydrogenator, 30.0 g (0.143 mol) of 2-methyl-3-nitrophenylmethyl acetate in 250 mL of methanol was hydrogenated in the presence of 0.5 g of palladium oxide on charcoal to give 25.0 g of 3-amino-2-methylphenylmethyl acetate.

(C) Preparation of 3-(2-furanyl)-2-methylphenylmethyl acetate

A stirred solution of 10.0 g (0.056 mol) of 3-amino-2-methylphenylmethyl acetate and 37.4 g (0.055 mol) of furan was heated to reflux, and 8.6 g (0.084 mol) of tert-butyl nitrite was added dropwise during 30 minutes. Upon complete addition, the reaction mixture was heated under reflux an additional 1.5 hours, then cooled, and 300 mL of heptane was added. The solution was filtered through 50 g of silica gel. The silica gel was washed with 400 mL of pentane. The wash and filtrate were combined and concentrated under reduced pressure to give a residual oil which was subjected to column chromatography on silica gel, eluting with toluene. The appropriate fractions were combined and concentrated under reduced pressure to give a residual oil. The oil was subjected to distillation under reduced pressure using a Kugelrohr distilling system to give 4.1 g of 3-(2-furanyl)-2-methylphenylmethyl acetate, b.p. 94±2° C./0.05 mm.

The nmr and ir spectra were consistent with the proposed structure.

(D) Hydrolysis of 3-(2-furanyl)-2-methylphenylmethyl acetate

This reaction was conducted in the manner of Example 8 Step 1E using 3.1 g (0.014 mol) of 3-(2-furanyl)-2-methylphenylmethyl acetate and 1.8 g (0.027 mol) of potassium hydroxide in 40 mL of methanol. The yield of 3-(2-furanyl)-2-methylphenylmethanol was 2.5 g, m.p. 48.5°–50° C.

The nmr and ir spectra were consistent with the proposed structure.

Step 2 Reaction of 3-(2-furanyl)-2-methylphenylmethanol with cis-3-(2-chloro-3,3,3-trifluoro-1-propenyl)-2,2-dimethylcyclopropanecarbonyl chloride This reaction was conducted in the manner of Example 3 Step 2, using 1.4 g (0.005 mol) of cis-3-(2-chloro-3,3,3-trifluoro-1-propenyl)-2,2-dimethylcyclopropanecarbonyl chloride, 1.0 g (0.005 mol) of 3-(2-furanyl)-2-methylphenylmethanol, and 0.5 g (0.006 mol) of pyridine in toluene. The yield of [3-(2-furanyl)-2-methylphenyl]methyl cis-3-(2-chloro-3,3,3-trifluoro-1-propenyl)-2,2-dimethylcyclopropanecarboxylate was 2.1 g, b.p. 150±2° C./0.05 mm.

The nmr and ir spectra were consistent with the proposed structure.

Analysis calc'd for $C_{21}CH_{20}ClF_3O_3$: C 61.10; H 4.88; Found: C 60.90; H 4.91.

EXAMPLE 12

Synthesis of [3-(2-furanyl)-2-methylphenyl]methyl cis-and cis,trans-3-(2,2-dichloroethenyl)-2,2-dimethylcyclopropanecarboxylate (Method A)

This compound was prepared in the manner of Example 3, Step 2, using 1.8 g (0.008 mol) of cis,trans-3-(2,2-dichloroethenyl)-2,2-dimethylcyclopropanecarbonyl chloride, 1.5 g (0.008 mol) of 3-(2-furanyl)-2-methylphenylmethanol, and 0.6 g (0.008 mol) of pyridine in 30 mL of toluene. The oily reaction product was subjected to column chromatography on silica gel, eluting with heptane:ethyl acetate (30:1). Early fractions from the column were combined and concentrated under reduced pressure to give 1.4 g of [3-(2-furanyl)-2-methylphenyl]methyl cis-3-(2,2-dichloroethenyl)-2,2-dimethylcyclopropanecarboxylate as an oil.

The nmr and ir spectra were consistent with the proposed structure.

Analysis calc'd for $C_{20}H_{20}Cl_2O_3$: C 60.77; H 5.10; Found: C 63.61; H 5.50.

The remaining fractions were combined and concentrated under reduced pressure to give an oil. The oil was subjected to a second column chromatography under the same conditions as above to give an additional 0.30 g of the cis-isomer. The remaining fractions were combined and concentrated under reduced pressure to give [3-(2-furanyl)-2-methylphenyl]methyl cis,trans-3-(2,2-dichloroethenyl)-2,2-dimethylcyclopropanecarboxylate.

The nmr and ir spectra were consistent with the proposed structure.

EXAMPLE 13

Synthesis of [2-methyl-3-(pyrazinyl)phenyl]methyl cis-3-(2-chloro-3,3,3-trifluoro-1-propenyl)-2,2-dimethylcyclopropanecarboxylate (Method A)

Step 1: Preparation of 2-methyl-3-(pyrazinyl)phenylmethanol (A) Preparation of 3-nitro-2-methylbenzenemethanol tetrahydropyranyl ether A solution of 100 g (0.598 mol) of 2-methyl-3-nitrophenylmethanol, 75.5 g (0.897 mol) of dihydropyran, and 15.0 g (0.06 mol) of the pyridinium salt of 4-methylbenzenesulfonic acid in 1 L of methylene chloride was stirred at ambient temperature for 24 hours. The reaction mixture was washed with two portions of 200 mL each of a saturated aqueous solution of sodium chloride, dried with magnesium sulfate, filtered, and the filtrate concentrated under reduced pressure to give a residual oil. The oil was subjected to column chromatography on silica gel, eluting with methylene chloride. The appropriate fractions were combined and concentrated under reduced pressure to give a residual oil. The oil was dissolved in 1 L of toluene, and was stirred in a Morton flask for 19 hours in the presence of 5 g of powdered Raney nickel. The mixture was filtered, and the filtrate concentrated under reduced pressure to give 147.8 g of 3-nitro-2-methylbenzenemethanol tetrahydropyranyl ether.

(B) Preparation of 3-amino-2-methylbenzenemethanol tetrahydropyranyl ether

This compound was prepared in the manner of Example 11, Step 1B using 40.0 g (0.159 mol) of 3-nitro-2-methylbenzenemethanol tetrahydropyranyl ether, 200 mL of methanol, and 1.25 g of palladium or charcoal. The yield of 3-amino-2-methylbenzenemethanol tetrahydropyranyl ether was 34.0 g.

The nmr spectrum was consistent with the proposed structure.

(C) Preparation of 2-methyl-3-(pyrazinyl)benzenemethanol tetrahydropyranyl ether A stirred solution of 50.0 g (0.624 mol) of pyrazine and 13.8 g (0.624 mol) of 3-amino-2-methylbenzenemethanol tetrahydropyranyl ether was warmed to 84° C.±6° C. and 9.6 g (0.094 mol) of t-butyl nitrite was added dropwise during 10 minutes. Upon complete addition, the reaction mixture was stirred at 85° C.±6° C. for 0.75 hours, then allowed to cool slowly to ambient temperature. The reaction mixture was dissolved in 100 mL of toluene, and subjected to column chromatography on silica gel, eluting with toluene-methylene chloride (3:1), methylene chloride, and finally ethyl acetate-methylene chloride (4:1). All the fractions were combined and subjected to a second column chromatography on silica gel, eluting with ethyl acetate-methylene chloride (1:19), ethyl acetate-methylene chloride (1:9), and ethyl acetate. The appropriate fractions were combined and concentrated under reduced pressure to give a residual oil. The oil was subjected to distillation under reduced pressure using a Kugelrohr distilling system to give 2.4 g of 2-methyl-3-(pyrazinyl)-benzenemethanol tetrahydropyranyl ether, b.p. 163° C.±3° C./0.04 mm.

The nmr spectrum was consistent with the proposed structure.

(D) Hydrolysis of 2-methyl-3-(pyrazinyl)benzenemethanol tetrahydropyranyl ether

A solution of 2.4 g (0.008 mol) of 2-methyl-3-(pyrazinyl)-benzenemethanol tetrahydropyranyl ether and 0.21 g of the pyridinium salt of 4-methylbenzenesulfonic acid in 35 mL of ethanol was warmed to 50° C.±5° C., and stirred for 24 hours. The reaction mixture was concentrated under reduced pressure, and the residue stirred for one hour with a mixture of 50 mL of methylene chloride and 50 mL of water. The organic layer was separated, dried, and concentrated under reduced pressure to give 1.6 g 2-methyl-3-(pyrazinyl)-phenylmethanol as an oily solid residue.

The nmr spectrum was consistent with the proposed structure.

Step 2: Reaction of
2-methyl-3-(pyrazinyl)phenylmethanol with
cis-3-(2-chloro-3,3,3-trifluoro-1-propenyl)-2,2-dimethylcyclopropanecarbonyl chloride The reaction was conducted in the manner of Example 3, Step 2 using 1.0 g (0.004 mol) of cis-3-(2-chloro-3,3,3-trifluoro-1-propenyl)-2,2-dimethylcyclopropanecarbonyl chloride, 0.8 g (0.004 mol) of 2-methyl-3-(pyrazinyl)phenylmethanol, and 0.4 g (0.005 mol) of pyridine in 30 mL of toluene. The yield of [2-methyl-3-(pyrazinyl)phenyl]methyl cis-3-(2-chloro-3,3,3-trifluoro-1-propenyl)-2,2-dimethylcyclopropanecarboxylate was 1.2 g, b.p. 170° C.±5° C./0.05 mm.

The nmr and ir spectra were consistent with the proposed structure.

Analysis calc'd for $C_{20}H_{20}ClF_3N_2O_2$: C, 58.19; H, 4.88; Found: C, 57.81; H 5.05.

EXAMPLE 14

Synthesis of [2-methyl-3-(pyrazinyl)phenyl]methyl cis-(2,2-dichloroethenyl)-2,2-dimethylcyclopropanecarboxylate (Method A)

This compound was prepared in the manner of Example 3, Step 2 using 0.91 g (0.004 mol) of cis-3-(2,2-dichloroethenyl)-2,2-dimethylcyclopropanecarbonyl chloride, 0.80 g (0.004 mol) of 2-methyl-3-(pyrazinyl)-phenylmethanol, and 0.8 g (0.01 mol) of pyridine in 30 mL of toluene. The yield of [2-methyl-3-(pyrazinyl)-phenyl]methyl cis-(2,2-dichloroethenyl)-2,2-dimethylcyclopropanecarboxylate was 1.42 g, b.p. 163° C.±5° C./0.04 mm.

The nmr and ir spectra were consistent with the proposed structure.

Analysis calc'd for $C_{20}H_{20}Cl_2N_2O_2$: C 61.39; H 5.15; Found: C 62.02; H 5.75.

EXAMPLE 15

Synthesis of [2-methyl-3-(pyridin-3-yl)phenyl]methyl cis-3-(2-chloro-3,3,3-trifluoro-1-propenyl)-2,2-dimethylcyclopropanecarboxylate (Method A)

Step 1: Preparation of 3-(3-pyridyl)phenylmethanol (A) Preparation of a mixture of 3-(3-chloro-2-methylphenyl)pyridine and 2-(3-chloro-2-methylphenyl)-pyridine In a Morton flask under an argon atmosphere a stirred solution of 75.0 g (0.530 mol) of 3-chloro-2-methylaniline in 419.2 g (5.3 mole) of pyridine was warmed to 80° C. At this temperature, 81.9 g (0.795 mol) of t-butyl nitrite was added dropwise during 1.5 hour. Upon complete addition, the reaction mixture was stirred at 80° C. for 16 hours, then poured into 500 mL ice water. The mixture was saturated with solid sodium chloride, and extracted with four portions of 300 mL each of diethyl ether. The organic extracts were combined and washed with 500 mL of a saturated aqueous solution of sodium chloride. The organic layer was dried with magnesium sulfate, filtered, and the filtrate concentrated under reduced pressure to give a residual oil. The oil was subjected to column chromatography on silica gel, eluting with methylene chloride-heptane (1:1), ethyl acetate, then ethanol-ethyl acetate (1:9). The appropriate fractions were combined and concentrated under reduced pressure to give 33.2 g of a black residual oil. The oil was subjected to a second column chromatography on silica gel, eluting with ethyl acetate-heptane (1:4). The appropriate fractions were combined and concentrated under reduced pressure to give a residual oil. The oil was subjected to distillation under reduced pressure using a Kugelrohr distilling system to give 7.9 g of a yellow oil, b.p. 110° C./0.075 mm; determined by nmr analysis to be 2-(3-chloro-2-methylphenyl)pyridine.

Analysis calc'd for $C_{12}H_{10}ClN$: C, 70.76; H 4.95; Found: C 71.20; H 5.23.

Other fractions from the second chromatography were combined and concentrated under reduced pressure to give a residual oil. The oil was subjected to distillation as above to give 2.9 g of a yellow oil, b.p. 110° C./0.025 mm; determined by nmr analysis to be 3-(3-chloro-2-methylphenyl)pyridine.

Analysis calc'd for $C_{12}H_{10}ClN$: C 70.76; H 4.95; Found: C 69.06; H 4.78.

(B) Preparation of 3-(3-cyano-2-methylphenyl) pyridine

A mixture of 7.5 g (0.012 mol) of 3-(3-chloro-2-methylphenyl)pyridine and 1.7 g (0.018 mol) of copper I cyanide in 1.45 g (0.018 mol) of pyridine was heated at 195° C. for 18 hours. The reaction mixture was cooled to 50° C., and 40 mL of methylene chloride was added with stirring. The mixture was placed in a separatory funnel, and 75 mL of methylene chloride and 75 mL of a 35% aqueous solution of ammonium hydroxide were added. The mixture was shaken for five minutes, then passed through a fiber glass filter paper. The layers were separated, and the aqueous layer was washed with two portions of 40 mL each of methylene chloride. The combined organic layers were washed with three portions of 40 mL each of a 35% aqueous solution of ammonium hydroxide. The organic layer was dried with magnesium sulfate, filtered, and the filtrate concentrated under reduced pressure to give 2.0 g of 3-(3-cyano-2-methylphenyl)pyridine.

The nmr and ir spectra were consistent with the proposed structure.

(C) Preparation of 2-methyl-3-(3-pyridyl)benzaldehyde

To a stirred solution of 2.0 g (0.01 mol) of 3-(3-cyano-2-methylphenyl)pyridine in 40 mL of toluene was added dropwise 11.5 mL (0.012 mol) of diisobutylaluminum hydride. Upon complete addition, the reaction mixture was stirred at ambient temperature for 16 hours, then at 50° C. for two hours. Methanol (10 mL) was added with stirring, and the resulting gelatinous mixture was cooled and stirred with 10 mL of aqueous 2 N sulfuric acid. The mixture was neutralized with an aqueous 5 N solution of sodium hydroxide, and extracted with two portions of 100 mL each of diethyl ether. The combined ether extracts were dried with magnesium sulfate, filtered, and the filtrate concentrated under reduced pressure to give 1.6 g of an oil. The oil was stirred for 16 hours in a saturated aqueous solution of sodium bisulfite, then extracted with two portions of 100 mL each of diethyl ether. The aqueous layer was neutralized with solid sodium bicarbonate, and extracted with three portions of 100 mL each of methylene chloride. The combined methylene chloride extracts were dried with magnesium sulfate, filtered, and the filtrate concentrated under reduced pressure to give 0.91 g of 2-methyl-3-(3-pyridyl)benzaldehyde.

The nmr spectrum was consistent with the proposed structure.

(D) Reduction of 2-methyl-3-(3-pyridyl)benzaldehyde

This reaction was conducted in the manner of Example 9, Step 1C using 0.9 g (0.005 mol) of 2-methyl-3-(3-pyridyl)-benzaldehyde and 0.17 g (0.005 mol) of sodium borohydride in 25 mL of ethanol. The yield of 2-methyl-3-(3-pyridyl)phenylmethanol was 0.78 g.

The nmr and ir spectra were consistent with the proposed structure.

Step 2: Reaction of
2-methyl-3-(pyridyl)phenylmethanol with cis-3-(2-chloro-3,3,3-trifluoro-1-propenyl)-2,2-dimethylcyclopropanecarbonyl chloride This reaction was conducted in the manner of Example 3, Step 2 using 1.02 g (0.004 mol) of cis-3-(2-chloro-3,3,3-trifluoro-1-propenyl)-2,2-dimethylcyclopropanecarbonyl chloride, 0.78 g (0.004 mol) of 2-methyl-3-(3-pyridyl)phenylmethanol, and 0.32 mL (0.004 mol) of pyridine in 25 mL of toluene. The yield of [2-methyl-3-(pyridin-3-yl)phenyl]methyl cis-3-(2-chloro-3,3,3-trifluoro-1-propenyl)-2,2-dimethylcyclopropanecarboxylate was 1.6 g, b.p. 160° C./0.05 mm.

The nmr and ir spectra were consistent with the proposed structure.

Analysis calc'd for $C_{22}H_{21}F_3ClNO_2$: C 62.34; H 5.00; Found: C 62.17; H 5.35.

EXAMPLE 16

Synthesis of [2-methyl-3-(pyridin-2-yl)phenyl]methyl cis-3-(2-chloro-3,3,3-trifluoro-1-propenyl)-2,2-dimethylcyclopropanecarboxylate (Method A)

Step 1: Preparation of
2-methyl-3-(2-pyridyl)phenylmethanol as an intermediate (A) Preparation of 2-(3-cyano-2-methylphenyl)pyridine This compound was prepared in the manner of Example 15, Step 1B using 1.2 g (0.009 mol) of 2-(3-chloro-2-methylphenyl)pyridine, 0.8 g (0.009 mol) of copper I cyanide, and 0.72 mL (0.009 mol) of pyridine. The yield of 2-(3-cyano-2-methylphenyl)pyridine was 0.83 g.

The ir spectrum was consistent with the proposed structure.

(B) Preparation of 2-methyl-3-(2-pyridyl)benzaldehyde

This compound was prepared in the manner of Example 15, Step 1C using 0.83 g of 2-(3-cyano-2-methylphenyl)pyridine and 4.7 mL (0.005 mol) of diisobutylaluminum hydride in 20 mL of toluene. The yield of 2-methyl-3-(2-pyridyl)benzaldehyde was 0.53 g.

The nmr and ir spectra were consistent with the proposed structure.

(C) Reduction of 2-methyl-3-(2-pyridyl)benzaldehyde

This reaction was conducted in the manner of Example 9, Step 1C using 0.5 g (0.003 mol) of 2-methyl-3-(2-pyridyl)-benzaldehyde and 0.1 g (0.003 mol) of sodium borohydride in 15 mL of ethanol. The yield of 2-methyl-3-(2-pyridyl)phenylmethanol was 0.46 g.

The nmr and ir spectra were consistent with the proposed structure.

Step 2: Reaction with
2-methyl-3-(pyridyl)phenylmethanol with cis-3-(2-chloro-3,3,3-trifluoro-1-propenyl)-2,2-dimethylcyclopropanecarbonyl chloride This reaction was conducted in the manner of Example 3, Step 2 using 0.58 g (0.002 mol) of cis-3-(2-chloro-3,3,3-trifluoro-1-propenyl)-2,2-dimethylcyclopropanecarbonyl chloride, 0.44 g (0.002 mol) of 2-methyl-3-(2-pyridyl)phenylmethanol, and 0.18 mL (0.002 mol) of pyridine in 30 mL of toluene. The yield of [2-methyl-3-pyridin-2-yl)phenyl]methyl cis-3-(2-chloro-3,3,3-trifluoro-1-propenyl)-2,2-dimethylcyclopropanecarboxylate was 0.8 g, b.p. 170° C./0.05 mm.

The nmr and ir spectra were consistent with the proposed structure.

Analysis calc'd for $C_{22}H_{21}F_3ClNO_2$: C 62.34; H 5.00; Found: C 63.79; H 5.60.

In the method aspect of this invention an effective insecticidal, miticidal or tickicidal amount of the compound of formula I wherein R is other than hydrogen is applied to the locus where control is desired, for example, to the insect itself, to the foliage or seeds of agricultural plants, or to surfaces on which the insect feeds. The compounds are useful for the control of household, veterinary, and crop pests and may be applied as technical material or as a formulated product.

Typical formulations include compositions of the active ingredient in combination with an agriculturally acceptable carrier or extender, preferably with a surface-active agent, and optionally with other active ingredients or adjuvants. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. An agriculturally acceptable carrier may comprise about 99.9% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier, for example, water. The concentration of the active ingredient in the use dilution may be in the range of about 0.01 to about 10% by weight. Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, etc.

In applying these compounds, whether alone or with other agricultural chemicals, an effective insecticidal amount of the active ingredient must be applied. While the application rate will vary widely depending on the choice of compound, the formulation and mode of application, the plant species being protected, and the planting density, a suitable use rate may be in the range of 0.005 to 3 kg./hectare, preferably 0.01 to amount 1 kg./hectare.

The compounds of this invention were tested for activity against various crop pests as follows:

Topical Application: The compounds of this invention were tested for insecticidal activity against various insect species selected from southern armyworm (*Spodoptera eridania*), Mexican bean beetle, (*Epilachna varivestis*), milkweed bug (*Oncopeltus fasciatus*), and cabbage looper (*Tricoplusia ni*) by applying to the second or third dorsal thoracic segment of each larvae a one microliter droplet containing 5 mg/mL of test compound in acetone (5000 ng/insect). The test was allowed to stand 24 hours after application and was then read to determine the percent kill. The test results are reported in Table IV below.

To determine the $LD_{50}$ of the compounds, the topical application test was repeated by applying various amounts of toxicant. Also included among the species tested against for this determination were tobacco budworm (*Heliothis virescens*), beet armyworm (*Spodoptera exigua*), and boll weevil (*Anthonomus grandis*). The resulting $LD_{50}$ values are reported in Table IV.

Foliar Application: The activity of some of the compounds of the invention against various test species selected from pea aphid (*Acyrthosiphon pisum*), twospotted spider mite (*Tetranychus urticae*), southern armyworm (*Spodoptera eridania*), Mexican bean beetle (*Epilachna varivestis*), and cabbage looper (*Tricoplusia ni*) was determined by foliar application of the test compound. The test materials were formulated as aqueous solutions containing 10% acetone and 0.25% acetylphenoxypolyethoxyethanol. Activity against pea aphid was determined on English fava bean plants the leaves of which were sprayed to runoff with various concentrations of test solution prior to infestation with adult aphids. Activity against twospotted spider mite was evaluated on pinto bean plants whose leaves were sprayed to runoff with various concentrations of test solution after infestation with adult mites. Activity against the remaining species was evaluated on pinto bean plants whose leaves were sprayed to runoff with various concentrations of test solution before infestation with the appropriate immature insects. Mortality was read approximately 48 hours after treatment. The results are reported in Table IV.

TABLE I
Novel Alcohols

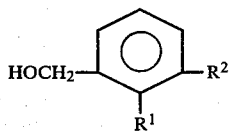

| Compound | $R^1$ | $R^2$ |
|---|---|---|
| I (a) | —H | 2-thienyl |
| (b) | —H | 3-thienyl |
| (c) | —H | 2-bromo-5-furanyl |
| (d) | —H | 2-furanyl |
| (e) | —CH$_3$ | 2-furanyl |
| (f) | —CH$_3$ | pyrazinyl |
| (g) | —CH$_3$ | 3-pyridinyl |

TABLE I-continued
Novel Alcohols

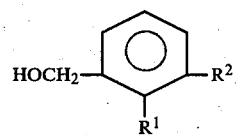

| Compound | $R^1$ | $R^2$ |
|---|---|---|
| (h) | —CH$_3$ | 2-pyridinyl |

TABLE II
Novel Insecticides

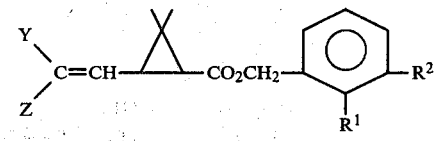

| Compound | Y + Z | $R^1$ | $R^2$ | Isomer |
|---|---|---|---|---|
| II (a) | Cl,Cl | —H | 2-thienyl | cis,trans |
| (b) | Cl,Cl | —H | 2-thienyl | cis |
| (c) | Cl,Cl | —H | 2-thienyl | trans |
| (d) | Cl,Cl | —H | 3-thienyl | cis |
| (e) | Cl,CF$_3$ | —CH$_3$ | 2-thienyl | cis |
| (f) | Cl,Cl | —CH$_3$ | 2-thienyl | trans |
| (g) | Cl,Cl | —CH$_3$ | 2-thienyl | cis |
| (h) | Cl,Cl | —CH$_3$ | 2-thienyl | 1R—cis |
| (i) | Br,Br | —CH$_3$ | 2-thienyl | cis |
| (j) | Cl,Cl | —H | 2-furanyl | cis |
| (k) | Cl,CF$_3$ | —H | 2-furanyl | cis |
| (l) | Cl,Cl | —H | 2-bromo-5-furanyl | cis |
| (m) | Cl,CF$_3$ | —CH$_3$ | 2-furanyl | cis |
| (n) | Cl,Cl | —CH$_3$ | 2-furanyl | cis |
| (o) | Cl,Cl | —CH$_3$ | 2-furanyl | cis,trans |
| (p) | Cl,CF$_3$ | —CH$_3$ | pyrazinyl | cis |
| (q) | Cl,Cl | —CH$_3$ | pyrazinyl | cis |
| (r) | Cl,CF$_3$ | —CH$_3$ | 3-pyridyl | cis |
| (s) | Cl,CF$_3$ | —CH$_3$ | 2-pyridyl | cis |

TABLE III
Intermediates

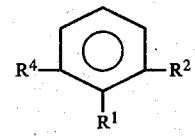

| Compound | $R^1$ | $R^2$ | $R^4$ |
|---|---|---|---|
| III (a) | —H | 2-thienyl | —CH$_3$ |
| (b) | —H | 3-thienyl | —CH$_3$ |
| (c) | —H | 2-thienyl | —CH$_2$Br |
| (d) | —H | 3-thienyl | —CH$_2$Br |
| (e) | —CH$_3$ | 2-thienyl | —Cl |
| (f) | —H | 2-thienyl | —CHO |
| (g) | —CH$_3$ | 2-thienyl | —CHO |
| (h) | —CH$_3$ | 2-thienyl | —CO$_2$H |
| (i) | —H | 3-thienyl | —CH$_2$OCOCH$_3$ |
| (j) | —H | 2-furanyl | —CH$_3$ |
| (k) | —H | 2-bromo-5-furanyl | —CH$_3$ |
| (l) | —H | 2-bromo-5-furanyl | —CH$_2$Br |
| (m) | —H | 2-bromo-5-furanyl | —CH$_2$OCOCH$_3$ |
| (n) | —H | 2-furanyl | —Br |
| (o) | —H | 2-furanyl | —CHO |
| (p) | —CH$_3$ | 2-furanyl | —CH$_2$OCOCH$_3$ |
| (q) | —CH$_3$ | pyrazinyl | —CH$_2$OTHP* |
| (r) | —CH$_3$ | 3-pyridyl | —Cl |
| (s) | —CH$_3$ | 2-pyridyl | —Cl |
| (t) | —CH$_3$ | 3-pyridyl | —CN |
| (u) | —CH$_3$ | 2-pyridyl | —CN |
| (v) | —CH$_3$ | 3-pyridyl | —CHO |

TABLE III-continued
Intermediates

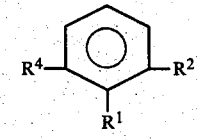

| Compound | $R^1$ | $R^2$ | $R^4$ |
|---|---|---|---|
| (w) | —$CH_3$ | 2-pyridyl | —CHO |

*THP = 2-tetrahydropyran

TABLE IV
Insecticidal and Acaricidal Activity

| Cpd[1] | Test Species[2] | Topical % Kill @ 5000 ng/insect | Topical $LD_{50}$ ng/insect | Foliar % Kill (ppm) |
|---|---|---|---|---|
| a | SAW | 100 | 148 | |
|   | CL  | 100 | 3649 | |
| b | SAW |     | 54 | 95(512) |
|   | CL  |     | 1275 | |
|   | MWB |     | 1715 | |
|   | MBB |     | 471 | 80(512) |
|   | PA  |     |     | 80(512) |
|   | TSM |     |     | 0(500) |
| c | SAW | 100 | 421 | |
|   | CL  | 0   |     | |
| d | SAW | 100 | 57  | |
|   | CL  |     | 2408 | |
|   | MWB | 95  | 1137 | |
|   | MBB | 100 | 73  | |
|   | BAW |     | 3010 | |
|   | PA  |     |     | 100(500) |
|   | TSM |     |     | 100(500) |
| e | SAW | 100 | 23  | 100(512) |
|   | CL  |     | 74  | 95(24) |
|   | MWB | 100 | 72  | 100(512) |
|   | MBB | 100 | 7   | |
|   | TBW |     | 43  | |
|   | BW  |     | 11  | |
|   | PA  |     |     | 100(512) |
|   | TSM |     |     | 100(512) |
| f | SAW | 100 | 155 | 100(512) |
|   | CL  |     |     | 100(120) |
|   | MWB | 100 | 238 | |
|   | MBB | 100 |     | 100(512) |
|   | PA  |     |     | 100(512) |
|   | TSM |     |     | 71(512) |
| g | SAW | 100 | 51  | 100(512) |
|   | CL  |     | 0.5 | 100(80) |
|   | BW  |     | 21  | |
|   | MWB | 100 | 234 | |
|   | MBB | 100 | 8   | 100(512) |
|   | TBW |     | 107 | |
|   | PA  |     |     | 100(512) |
|   | TSM |     |     | 0(64) |
| h | SAW | 100 | 22  | 100(6.5) |
|   | CL  |     | 136 | 90(16) |
|   | MWB | 100 | 64  | |
|   | MBB | 100 | 9   | 95(16) |
|   | TBW |     | 38  | |
|   | PA  |     |     | 100(500) |
|   | TSM |     |     | 100(500) |
| i | SAW | 100 | 55  | 95(16) |
|   | CL  |     | 371 | 70(32) |
|   | MWB | 100 | 132 | |
|   | MBB | 100 | 20  | 90(32) |
|   | TBW |     | 177 | |
|   | PA  |     |     | 100(500) |
|   | TSM |     |     | 90(500) |
| j | SAW | 100 | 377 | 100(512) |
|   | MWB | 0   |     | |
|   | MBB | 30  |     | 50(512) |
|   | PA  |     |     | 40(500) |
|   | TSM |     |     | 0(500) |
| k | SAW | 100 | 366 | 100(512) |
|   | MWB | 40  |     | |
|   | MBB | 90  | 510 | 100(512) |
|   | PA  |     |     | 100(512) |
|   | TSM |     |     | 0(64) |
| l | SAW | 100 | 1819 | 100(512) |
|   | MWB | 0   |     | |
|   | MBB | 35  |     | 80(512) |
|   | PA  |     |     | 75(512) |
|   | TSM |     |     | 0(64) |
| m | SAW | 100 | 56  | 100(500) |
|   | CL  |     | 149 | |
|   | MWB | 100 | 286 | |
|   | MBB | 100 | 43  | 75(64) |
|   | TBW |     | 46  | |
|   | PA  |     |     | 100(500) |
|   | TSM |     |     | 0(16) |
| n | SAW | 100 | 73  | 100(500) |
|   | CL  |     | 341 | |
|   | MWB | 100 | 1140 | |
|   | MBB | 100 | 72  | 40(64) |
|   | TBW |     | 92  | |
|   | PA  |     |     | 100(64) |
|   | TSM |     |     | 0(16) |
| o | SAW | 100 | 146 | 100(500) |
|   | CL  |     | 536 | |
|   | MWB | 100 | 450 | |
|   | MBB | 100 | 86  | 45(64) |
|   | TBW |     | 45  | |
|   | PA  |     |     | 100(500) |
|   | TSM |     |     | 0(16) |
| p | SAW | 90  | 1948 | 100(500) |
|   | MWB | 100 | 1050 | |
|   | MBB | 100 | 93  | 80(64) |
|   | PA  |     |     | 100(500) |
|   | TSM |     |     | 100(500) |
| q | SAW | 90  | 2387 | 85(500) |
|   | MWB | 90  | 4915 | |
|   | MBB | 90  | 269  | 55(64) |
|   | PA  |     |     | 100(500) |
|   | TSM |     |     | 0(16) |
| r | SAW | 100 | 2626 | 100(500) |
|   | MWB | 100 | 1047 | |
|   | MBB |     | 863  | 25(64) |
|   | PA  |     |     | 95(500) |
|   | TSM |     |     | 0(16) |
| s | SAW | 100 | 60   | 100(500) |
|   | MWB | 100 | 607  | |
|   | MBB | 100 | 38   | 60(64) |
|   | PA  |     |     | 100(500) |
|   | TSM |     |     | 80(500) |

[1] See Table II for compound identification.
[2] SAW — southern armyworm
CL — cabbage looper
MWB — milkweed bug
MBB — Mexican Bean Beetle
BAW — beet armyworm
TBW — tobacco budworm
BW — boll weevil
PA — pea aphid
TSM — twospotted spider mite

I claim:

1. A compound of the formula

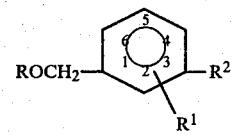

wherein $R^1$ is hydrogen, halogen, lower alkyl, or trihalomethyl; $R^2$ is a thiophene, furan, pyrazine, or pyridine ring which may be substituted with one or more halogen atoms or lower alkyl groups; and R is hydrogen.

2. The compound of claim 1 wherein $R^2$ is an unsubstituted thiophene, furan, pyrazine, or pyridine ring.

3. The compound of claim 2 wherein $R^1$ is a methyl group, and is positioned at C-2 of the phenyl ring.

* * * * *